United States Patent [19]

Anderson

[11] 4,236,520
[45] Dec. 2, 1980

[54] FLUID DRAIN OR INJECTION TUBE FOR AN ANIMAL'S UDDER

[76] Inventor: Mark L. Anderson, R.R. 2, Elmwood, Wis. 54740

[21] Appl. No.: 965,923

[22] Filed: Dec. 4, 1978

[51] Int. Cl.³ .......................................... A61M 25/00
[52] U.S. Cl. .............................. 128/348; 119/14.21; 128/343
[58] Field of Search ................... 128/348, 350 R, 341, 128/343; 119/14.19, 14.2, 14.21

[56] References Cited

U.S. PATENT DOCUMENTS

| | | | |
|---|---|---|---|
| 1,688,795 | 10/1928 | Aas | 128/348 |
| 1,797,339 | 3/1931 | Gudman-Hoyer | 119/14.21 |
| 2,704,076 | 3/1955 | Larson | 128/348 |
| 3,058,472 | 10/1962 | Thornton | 128/348 |
| 3,071,139 | 1/1963 | Nicholson | 128/350 R |

FOREIGN PATENT DOCUMENTS 914131 12/1962 United Kingdom .................... 128/343

Primary Examiner—Dalton L. Truluck
Attorney, Agent, or Firm—Edward H. Loveman

[57] ABSTRACT

A fluid drain or injection tube for insertion into a teat of an animal's udder has an elongated body with closed and open opposite ends, and with an axial bore terminating at the open end. The body has a first cylindrical section terminating in a blunt, rounded tip to facilitate entry into the teat. Elongated slots in this section communicate with the bore to pass fluid into and out of the bore. The body has an intermediate section of enlarged diameter formed with oppositely tapered portion for engaging in a passage in the teat. A radial annular flange serves as a stop element to limit insertion of the tube into the teat. A second cylindrical section of enlarged diameter at the open end of the tube receives a plug connected by a flexible strap with the tube. A tapered portion of the bore at the intermediate section frictionally grips the tapered tip of a medicament applicator inserted into the tube.

3 Claims, 5 Drawing Figures

FLUID DRAIN OR INJECTION TUBE FOR AN ANIMAL'S UDDER

This invention relates to a fluid drain or injection tube for an animal's udder, and more particularly concerns an improved flexible tube adapted for insertion in a teat and constructed to engage a syringe for draining fluid from an udder or for injecting medicament into the udder.

Tubes heretofore used for draining animal udders and for treating such conditions as mastitis, have generally been rigid metal or glass members, with smooth sides and a central passage terminating in openings at opposite ends of the tube. This simple construction has caused a number of difficulties in general usage. The inflexibility of the tube makes it difficult to pass through a teat passage which is not straight. The smooth sided tube tends to slip out of the teat. The narrow passage in the tube makes it difficult to insert medicaments into the udder. The open outer end of the tube permits leakage of the medicament if the tube is left in the teat. The rim of the opening at the inner end of the tube tends to catch on tissue in the passage of the teat making insertion difficult. Also the opening at the inner end of the tube often becomes blocked so milk and fluids cannot drain out of the udder.

The present invention is directed at overcoming the above and other difficulties and disadvantages of prior udder drain tubes. According to the invention there is provided a small, laterally bendable tube made of smooth, molded, high impact polystyrene or other suitable plastic. The tube is light in weight, small in size, and inexpensive to manufacture so that it can be thrown away after a single use. The tube has open and closed opposite ends. It has a narrow cylindrical section formed with a rounded, closed tip which readily enters the passage in a teat. Elongated lateral openings are formed in opposite sides of this cylindrical section, spaced axially of the tube and communicating radially with the central bore in the tube. These openings permit flow of fluid readily from the tube to the teat passage and from the teat passage to the axial bore of the tube.

The tube is formed near its open end with an annular, radial flange of enlarged diameter which serves as a stop element to limit insertion of the tube into a teat. A tapered reentrant intermediate section of the tube near the flange engages the wall of the teat passage and helps hold the tube in the teat. The tube may have a cylindrical portion adjacent the flange and a cylindrical section of larger diameter at the open end of the tube. This cylindrical section has a wide cylindrical bore portion adapted to receive the cylindrical end of a medicament applicator. A tapered plug may be connected to the side of the tube by an integral, flexible strap. This plug can be inserted snugly into the cylindrical open end portion of the axial bore to close the open end of the tube and prevent medicaments from leaking out of the udder through the teat in which the tube is inserted. The bore of the tube has a tapered portion in the intermediate tube section communicating with the bore portion in the narrow cylindrical tube section. The tapered bore portion is adapted to engage the tapered end of a syringe in a sung friction fit for removing milk and other fluids by suction from the udder or for injecting fluid medicament into the teat and udder.

These and other objects and many of the attendant advantages of this invention will be readily appreciated as the same becomes better understood by reference to the following detailed description when considered in connection with the accompanying drawings in which.

Figures 1, 2, 3, 4, 5:
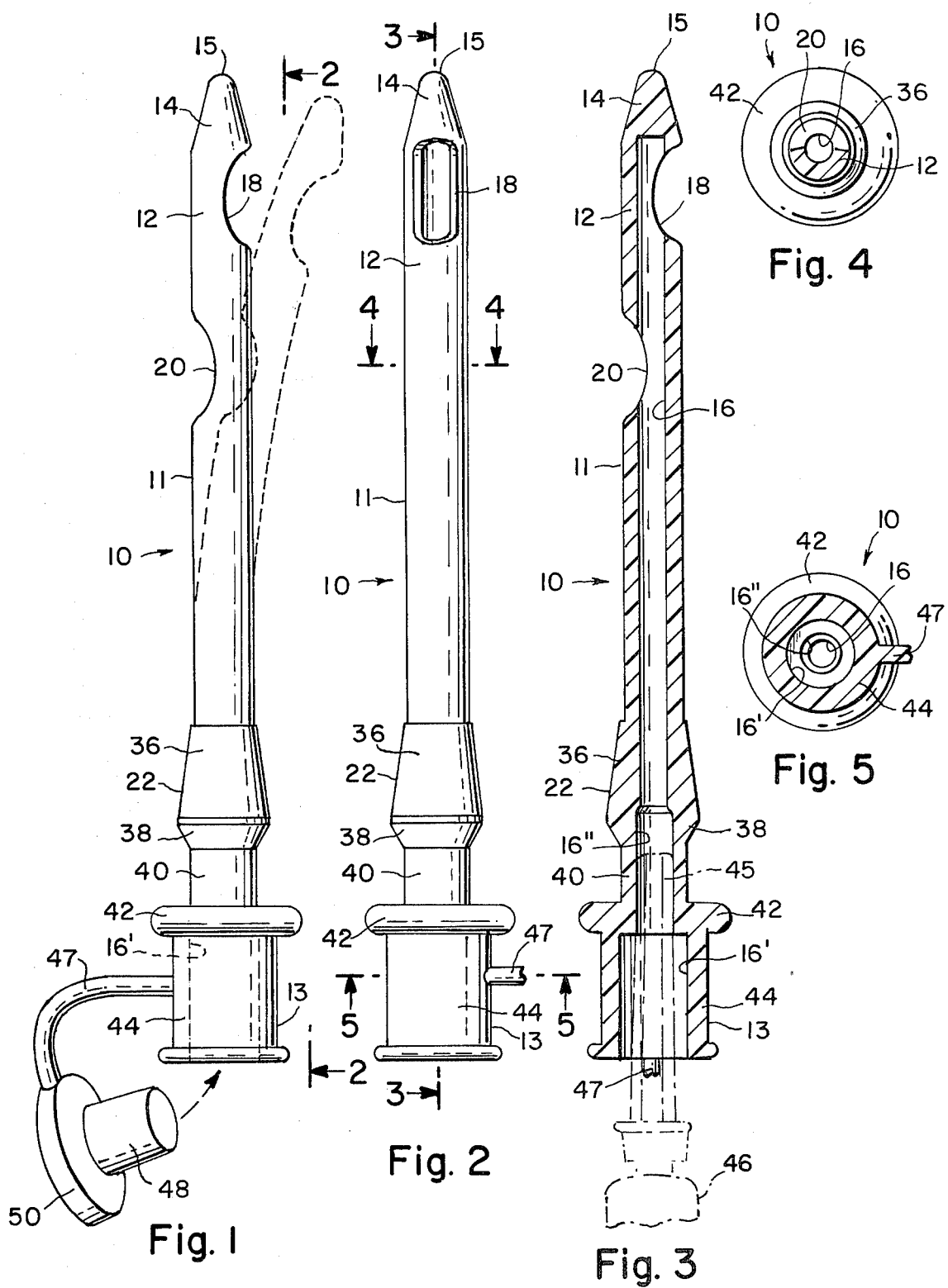
FIG. 1 is a side elevational view of a fluid drain and injection tube embodying the invention.
FIG. 2 is a side elevational view of the tube rotated 90° and taken along line 2—2 of FIG. 1.
FIG. 3 is an axial sectional view taken along line 3—3 of FIG. 2.
FIG. 4 and FIG. 5 are cross sectional views taken along lines 4—4 and 5—5 respectively of FIG. 2.

Referring now to the drawing wherein like reference characters designate like or corresponding parts throughout, there is illustrated in FIGS. 1-4, a fluid injection and drain tube, generally designated as reference numeral 10 which has an elongated tubular body 11 formed with open and closed opposite ends 13 and 15 respectively. The body 11 has a first cylindrical section 12 terminating at the closed end 15 of the tube 10 in a solid, rounded, tapered tip 14. The tapered tip 14 facilitates insertion of the tube 10 into the passage of a teat.

Inside the tube 10 is an axial bore 16. Communicating radially with the bore 16 are two elongated slots or openings 18, 20 spaced axially apart and open at opposite sides of the cylindrical section 12. The cylindrical section 12 is bendable laterally, although the tube 10 is radially stiff. The cylindrical section 12 is integral at the open end 13 with an intermediate body section 22 of enlarged diameter. The intermediate body section 22 has a tapered portion 36 integral with and adjacent to another portion 38 which is tapered oppositely from the portion 36 in a reentrant fashion. A cylindrical portion 40 is axially aligned with and adjacent to the tapered portion 38. This construction enables the end of a teat to grip the intermediate section 22 frictionally and thus retain the tube 10 in the teat. Fluid may readily pass from the passage in the teat to the bore 16 and vice versa via the openings 18, 20.

The tube 10 has a radial annular flange 42 of further enlarged diameter which serves as a stop element to limit axial insertion of the tube 10 into a teat. Extending beyond the flange 42 at the open end 13 of the tube 10 may be a cylindrical end section 44 which serves as a handle to grip the tube for insertion and removal. The end section 44 has a cylindrical bore portion 16' communicating with a tapered bore portion 16" within the intermediate section 22, and the tube portions 36, 38 and 40. The tapered bore portion 16" communicates with the cylindrical part of the bore 16 in the tube 12. The cylindrical bore portion 16' may receive the cylindrical end of a medicament applicator or a syringe 46 which have a respective tapered end 45 in a snug friction fit in the tapered bore 16", as indicated by dotted lines in FIG. 3, to facilitate injection of a medicament through tube 10 into the udder.

The tube 10 is provided with an end cap or plug 48, which is connected to a side of the tube section 44 by an integral, flexible strap 47 secured to an annular flanged head 50 of the cap 48. The cap 48 is tapered to close the bore 16" with a snub friction fit and prevent medication from leaking out of the teat and the tube 10, when the cap is inserted into the bore 16'. The cap 48 can readily be removed from the bore 16' as shown in FIG. 1.

The cylindrical section 12 is laterally bendable as shown by dotted lines in FIG. 1. Thus, the cylindrical section 12 can pass along a curved passage in a teat. The tube 10 is longitudinally and radially rigid and dimensionally stable. The entire tube 10 and the cap 48 are made of a chemically stable sterilizable plastic material. Since it is inexpensive to manufacture by mass production methods and machinery, the tube 10 may be discarded after each use.

In a typical construction for use with a cow's udder, the cylindrical section 12 may be about 1½ inches long. Overall the tube 10 may be about 2¼ inches long. The diameter of the cylindrical section 12 may be about 0.14 inches. The cylindrical bore 16 may be about 0.08 inches in the cylindrical section 12. The maximum diameter of the intermediate section at the junction of tapered portions 36 and 38 may be about 0.22 inches. The flange 42 may be about 0.36 inches in maximum diameter. This small handy size of the tube 10 is ideally suited for the purposes intended when used with teats of conventional size.

The tube 10 is very light in weight. It may remain in place in a teat for days at a time to allow time for the injected medicament to take effect. It is safe, sanitary, and foolproof.

It should be understood that the foregoing relates to only a preferred embodiment of the invention, which has been by way of example only, and that it is intended to cover all changes and modifications of the example of the invention herein chosen for the purposes of the disclosure, which do not constitute departures from the spirit and scope of the invention.

What is claimed is:

1. A fluid drain or injection tube of smooth plastic material for insertion in a teat of an animal's udder, comprising an elongated laterally bendable, rigid tubular body with a closed end and an open opposite end, and with an axial bore in said body terminating at said closed end and open at said open end, said body comprising:

a first cylindrical section terminating in a rounded tip at said closed end to facilitate entry into a teat of an udder, with axially elongated and axially spaced slot-like openings on opposite sides of said cylindrical section communicating with said bore to pass fluid into and out of said bore, an intermediate tapered imperforate section of enlarged diameter axially aligned with and integral with said first cylindrical section, said tapered imperforate section having two oppositely tapered portions, the first tapered portion extending axially outwardly from said enlarged diameter to a further enlarged diameter and the second tapered section extending axially inwardly from said further enlarged diameter to said enlarged diameter in reentrant fashion for retaining the same in said teat, a body section of greater enlarged diameter then said further enlarged diameter adjacent to said intermediate tapered imperforate section serving as a stop element to limit axial insertion of said body into said teat, said body section having a second cylindrical section at said open end of said body serving as a handle to facilitate insertion of said body into said teat and removal therefrom, said bore having, a first cylindrical portion in said first cylindrical section, a second cylindrical portion in said second cylindrical section wider in diameter than said first cylindrical portion for receiving a cylindrical end of a medicament applicator, and a tapered portion in said intermediate section for frictionally gripping a tapered end of said medicament applicator when inserted into said body through said open end thereof; and a plug connected by an integral flexible strap to said body for insertion into said second cylindrical portion to close the same and retaining fluid in said teat.

2. A tube as defined in claim 1, wherein said body is approximately 2¼ inches in length, and said first cylindrical section is approximately 1½ inches in length.

3. A tube as defined in claim 2, wherein the diameter of said first cylindrical section is approximately 0.14 inches, and wherein the maximum diameter of said intermediate section is approximately 0.22 inches.

* * * * *